United States Patent [19]

Gildersleeve et al.

[11] Patent Number: 5,456,659
[45] Date of Patent: Oct. 10, 1995

[54] SPLINT FOR A JOINT OF THE BODY HAVING AN ADJUSTABLE FLEXION ANGLE

[75] Inventors: Richard E. Gildersleeve, Escondido; Keith L. Cassford, San Diego; Jason L. Constable, Vista, all of Calif.

[73] Assignee: Smith & Nephew Donjoy Inc., Carlsbad, Calif.

[21] Appl. No.: 265,425

[22] Filed: Jun. 24, 1994

Related U.S. Application Data

[63] Continuation-in-part of Ser. No. 89,015, Jul. 9, 1993, Pat. No. 5,385,534.

[51] Int. Cl.$^6$ ............................................. A61F 5/00
[52] U.S. Cl. .................... 602/15; 602/16; 602/5; 602/20; 602/23; 602/26
[58] Field of Search ............................ 602/5, 6, 12, 15, 602/16, 20, 23, 26; 128/870, 877, 878, 882

[56] References Cited

U.S. PATENT DOCUMENTS

| | | |
|---|---|---|
| 2,409,195 | 10/1943 | Crawford . |
| 3,496,934 | 2/1970 | Anderson . |
| 3,624,745 | 11/1971 | Bowers . |
| 3,653,378 | 4/1972 | Reuther . |
| 3,695,258 | 10/1972 | Castle . |
| 3,850,167 | 11/1974 | Seeley . |
| 3,853,123 | 12/1974 | Moore . |
| 3,896,799 | 7/1975 | Seeley . |
| 4,041,940 | 8/1977 | Frankel et al. . |
| 4,111,194 | 9/1978 | Cox et al. . |
| 4,209,011 | 6/1980 | Peck et al. . |
| 4,383,526 | 5/1983 | Robins . |
| 4,520,806 | 5/1985 | Miller . |
| 4,598,702 | 7/1986 | Lilla .......................................... 602/4 |
| 4,753,240 | 6/1988 | Sparks . |
| 5,024,216 | 6/1991 | Shiono . |
| 5,195,944 | 3/1993 | Schlogel . |

*Primary Examiner*—Linda C. M. Dvorak
*Attorney, Agent, or Firm*—Rodney F. Brown

[57] ABSTRACT

A splint and a kit from which the splint is assembled include a plurality of components having a planar configuration for compact storage when in the kit, but having a three-dimensional configuration conforming to the desired body contours when the splint is assembled. The individual planar kit components include a rigid support member, a pad for cushioning the support member against the body, a plurality of belts for securing the support member to the body, a pair of flexion members for fixedly retaining the flexion angle of the support member, and one or more straps flexibly connecting the flexion members to the support member. The support member is an elongated surface having two longitudinal grooves formed therein that act as contour joints, and two slits formed therethrough perpendicular to the grooves that act as flexion joints. The joints remain fully extended and flat in the kit, but when the splint is assembled from the kit, the contour joints are flexed to impart a U-shape to the support member conforming to the desired contour of the body. The flexion joints are likewise flexed to a selected flexion angle for the body joint and the flexion members are fastened to the support member surface across the slits to fix the flexion angle.

31 Claims, 5 Drawing Sheets

SPLINT FOR A JOINT OF THE BODY HAVING AN ADJUSTABLE FLEXION ANGLE

This is a continuation-in-part patent application of U.S. patent application Ser. No. 08/089,015 filed on Jul. 9, 1993, now U.S. Pat. No. 5,385,534.

TECHNICAL FIELD

The present invention relates generally to a splint for immobilizing the joint of a selected jointed body part, and more particularly to a splint having an adjustable flexion angle corresponding to a desired flexion angle of the immobilized joint.

BACKGROUND OF THE INVENTION

A splint is used primarily as a short-term means for immobilizing a body part following an injury thereto. Where the injury is minor, such as a slight joint sprain, requiring a relatively short treatment period, the splint can serve as the primary treatment means for the duration of the treatment period. Where the injury is more severe, however, such as a broken bone or a torn ligament, the splint usually serves as an immediate, but only temporary, treatment means until more long-term treatment of the injured body part can be administered, often in the form of a brace or cast. Temporary splints are commonly employed under emergency post-trauma conditions in locales remote from treatment facilities.

Whether the splint provides primary or temporary treatment, effective immobilization of the affected body part requires a close fit between the splint and the body part. Splints, however, are usually produced in only one or a few generalized sizes because of the disposable nature of splints and the difficulty in stocking a large range of splint sizes and individually sizing each user during emergency applications. Accordingly, splints are preferably designed to be at least somewhat adjustable to the specific size requirements of the user with the object of enhancing the fit of the splint.

Unfortunately, splints, which are rigid by necessity, do not readily adapt to the contours of the body, and particularly to the contours of limbs encompassing flexible joints that frequently require splinting. Therefore, prior art designs for splints and other joint immobilizing devices have balanced a trade-off between closeness of fit and degree of rigidity.

U.S. Pat. No. 3,853,123 teaches a knee brace formed from a resilient shell that wraps around the leg and knee joint to restrain flexion of the knee joint. The shell is maintained in place by a plurality of pliable straps drawn tight to encircle the leg and shell. Although the brace provides a snug fit with the leg, its resilient components do not always provide sufficient rigidity and corresponding immobility for post-trauma applications. In addition, the brace does not permit setting the knee joint at a flexion angle other than the angle defined by the relatively straight axis of the leg.

U.S. Pat. No. 4,041,940 teaches a knee immobilizer that has a rigid U-shaped shell conforming to the leg of the user and having a slight flexion angle built into the shell about the knee joint. Although the shell provides a relatively close fit with the leg, its three-dimensional configuration renders the device impractical for emergency field applications. The device is difficult to store or transport at remote trauma sites due to the excessive bulk of the configuration. Additionally, the device is limited to one flexion angle which may not always be optimum for the particular application.

U.S. Pat. No. 2,409,195 discloses a splint having longitudinal joints formed therein for conformance of the splint to the substantially cylindrical lateral contour of the patient. The splint is further provided with lateral joints to conform the splint to the somewhat bowed longitudinal contour of the patient. However, the joints diminish the effectiveness of the splint because the joints cannot be fixed, and accordingly are easily flexed with movement of the patient.

U.S. Pat. No. 3,653,758 discloses a splint having a flexion joint formed therein for conformance of the splint to a desired flexion angle of the knee joint. The flexion joint of the splint can be fixed at a desired flexion angle by tightening a plurality of bolts at the joint. This task, however, is cumbersome, particularly in emergency situations where the necessary tools may not be available.

Accordingly, it is an object of the present invention to overcome the problems set forth above with respect to prior art splints and joint immobilizers. In particular, it is an object of the present invention to achieve a high degree of immobilization for an injured body part by providing a splint that is substantially rigid, yet is close-fittingly adaptable to various body sizes.

It is another object of the present invention to provide a splint for a body joint that can be rapidly and fixedly set to a desired angle of joint flexion. It is a further object of the present invention to provide a splint for a body joint that can be readily assembled from a kit without any tools, wherein the kit is highly compact and stackable enabling practical storage and transportation of a relatively large splint inventory at remote trauma sites or treatment centers.

SUMMARY OF THE INVENTION

The present invention is both a kit for assembling a splint, and the splint assembled from the kit. The assembled splint comprises a support member for a jointed body part, such as an arm or a leg. The support member has an elongated planar configuration that is fabricated from a substantially rigid material. A pair of spaced-apart grooves are longitudinally formed on the inner face of the support member surface segmenting the support member into a series of three interconnected panels, i.e., a bottom panel and a pair of side panels. The grooves, which are the lines of intersection between the panels, function as contour joints about which the panels are pivoted to provide the support member with a U-shaped configuration. Accordingly, the side panels engage the medial and lateral sides of the selected body part (with reference to the joint) and the bottom panel engages the posterior side of the body part. The top of the support member remains open, leaving the anterior side of the body part exposed.

The support member is provided with a slit formed through each side panel in substantially perpendicular alignment with the longitudinal axis of the bottom panel. Each slit extends from an opposite longitudinal edge of the support member to an adjacent groove. When the support member is positioned on a selected body part, the position of the slits aligns with the joint thereof. The slits function as flexion joints about which the support member is adustably pivoted to a desired flexion angle. The degree of pivotal separation the slits undergo defines the flexion angle of the support member and, correspondingly, the flexion angle of the splinted joint. Thus, the support member immobilizes the jointed body part with the joint maintained at the desired flexion angle.

A substantially rigid flexion member is further provided in association with each slit to fixedly maintain the desired flexion angle. Each flexion member is flexibly connected to the bottom panel by means of a strap and is fixably fastened to the side panel on each side of the slit by means of an adhesive or the like.

In accordance with a first embodiment of the splint, each flexion member has a tapered configuration with the widened base of the flexion member positioned proximal to the bottom panel of the support member such that the flexion member tapers away from the bottom panel. This orientation of the flexion member enables adjustment of the desired flexion angle to a positive value, which has particular utility to immobilization of the knee joint when the splint is positioned on the leg. In accordance with a second embodiment of the present invention, the flexion member likewise has a tapered configuration. The widened base of the flexion member, however, is positioned distal, rather than proximal, to the bottom panel of the support member such that the flexion member tapers toward the bottom panel. This orientation of the flexion member enables adjustment of the desired flexion angle to a negative value which has particular utility to immobilization of the elbow or ankle joint when the splint is positioned on the arm or leg, respectively.

The splint further comprises a pliant pad positioned over the inner face of the support member to enhance the comfort of the user and to ensure the fit of the splint with the body part. The pad can have slits formed therethrough positioned in correspondence with the slits in the support member. The pad slits facilitate flexion of the pad in correspondence with flexion of the support member. The splint is secured to the body by a plurality of pliant belts threaded through a plurality of loops integral with the support member, thereby enclosing the splint around the body part.

The flat stackable kit from which the above-described splint is assembled has substantially the same components as the splint, but the components are in an unassembled configuration. When unassembled, the support member and pad are maintained in a planar configuration with the contour and flexion joints fully extended to zero degrees. The flexion members are positioned in substantially the same plane as the support member and are maintained in flexible connection with the support member, but are not fixably fastened to the support member. The adhesive fastener on the support or flexion member is covered with a removable nonadhesive shield to avoid accidental fixable fastening of the flexion members to the support member until the kit components are prepared for assembly. The unassembled configuration of the kit components enables compact storage of multiple kits stacked atop one another.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
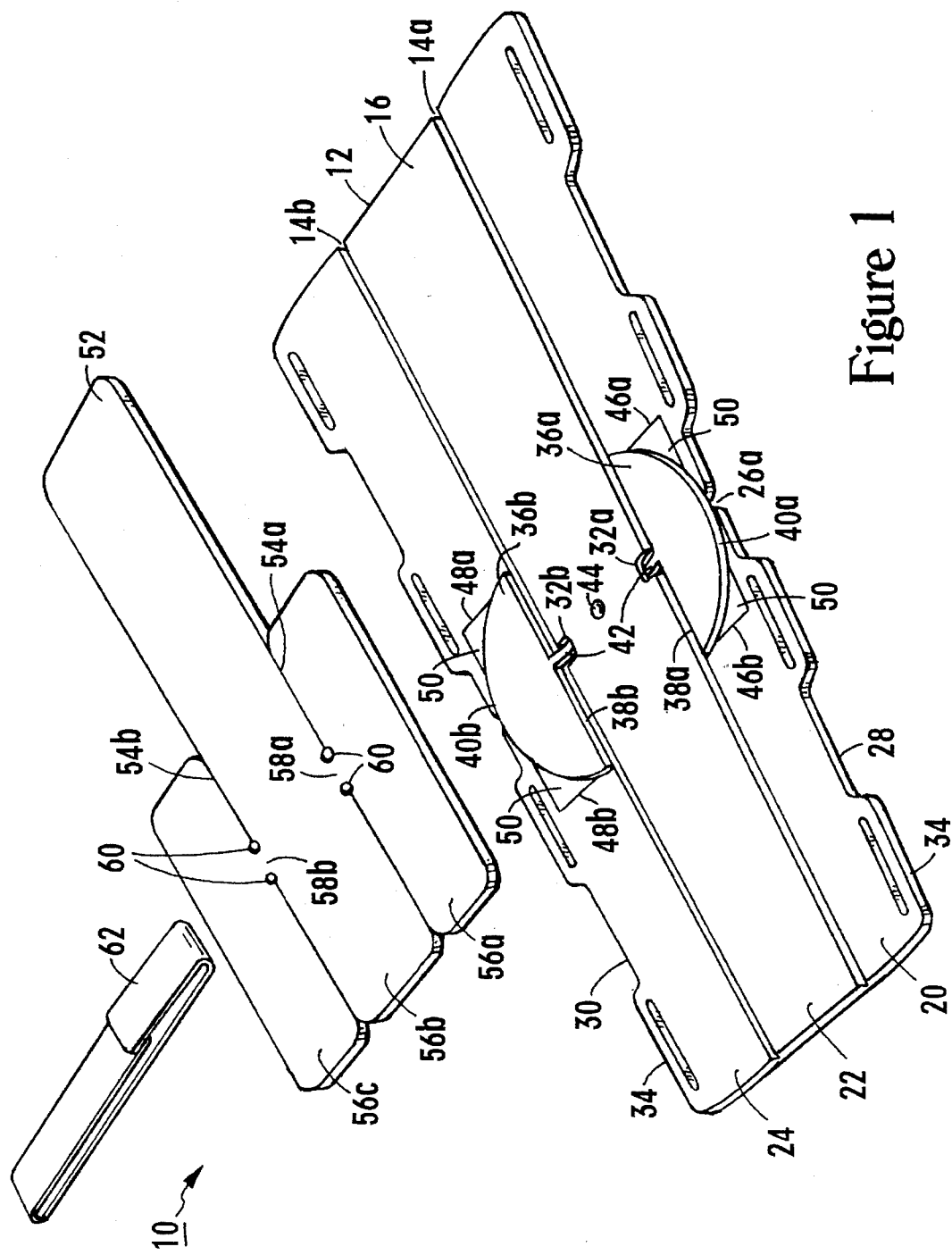
FIG. 1 is an exploded top perspective view of an unassembled flat stackable kit of the present invention from which a splint is assembled.

An unassembled flat stackable kit of the present invention, from which a splint is assembled, is shown and described with reference to FIGS. 1 and 2, wherein the kit is generally designated 10. The kit 10 is particularly applicable to knee splints that fit onto the leg of a user for immobilizing the knee joint as described hereafter. It is apparent to one skilled in the art, however, that the kit 10 can alternatively be adapted to body parts encompassing a flexible body joint other than the knee in accordance with the instant teaching. Thus, the kit 10 is likewise applicable to splints of other joints without substantial modification, such as elbow splints that fit onto the arm of a user for immobilizing the elbow joint and ankle splints that fit onto the leg of a user for immobilizing the ankle joint.

The kit 10 comprises a support member 12 fabricated from a sheet of a disposable lightweight material that is substantially stiffened or rigid to the extent that the sheet exhibits only a limited degree of elasticity and deformability at its full thickness when subjected to manually applied forces. The sheet, however, exhibits a degree of inelastic deformability at lesser thicknesses under manually applied forces. Materials satisfying these criteria at a full thickness on the order of about 3/32 inch or more include certain metals and hard plastics, such as polyethylene and others well known to the skilled artisan. The support member 12 can be cut from the desired sheet of material in a single unitary piece to produce the support member 12 having an elongated planar configuration approximating the length of the leg being splinted, although preferably somewhat shorter.

A pair of linear longitudinal grooves 14a, 14b are provided in the inner face 16 of the surface of the support member 12 and extend the length of the inner face 16. The grooves 14a, 14b are formed by scoring the inner face 16 without completely penetrating through the support member 12 to the outer face 18 of the surface of the support member 12. Accordingly, the support member 12 has a substantially reduced thickness at the grooves 14a, 14b rendering the support member 12 more flexible and inelastically deformable at the position of the grooves 14a, 14b as compared to the remainder of the support member 12 having a full thickness. The grooves 14a, 14b segment the support member 12 into three interconnected panels consecutively referenced as a first side panel 20, a bottom panel 22, and a second side panel 24. The groove 14a defines the line of intersection between the first side panel 20 and the bottom panel 22, and the groove 14b defines the line of intersection between the second side panel 24 and the bottom panel 22.

A pair of linear slits 26a, 26b are provided in the support member 12 completely penetrating the support member 12 from the inner to the outer faces 16, 18. The slits 26a, 26b are intermediately positioned on the longitudinal edges 28, 30 of the support member 12, respectively, and are aligned approximately perpendicular to the longitudinal axis of the support member 12 as well as approximately perpendicular to the longitudinal edges 28, 30 and the grooves 14a, 14b. The slits 26a, 26b extend from the respective longitudinal edges 28, 30 to about the respective grooves 14a, 14b of the support member 12. Cut-outs in the support member 12, termed expansion apertures 32a, 32b, are provided at the junction of the slits 26a, 26b and the grooves 14a, 14b. A plurality of belt loops 34 integral with the support member 12 are also provided along the longitudinal edge 28 and correspondingly along the longitudinal edge 30 of the support member 12.

The kit 10 further comprises a pair of flexion members 36a, 36b associated with the slits 26a, 26b, respectively. The flexion members 36a, 36b have a planar, tapered configuration. In accordance therewith, each flexion member 36a, 36b has a planar surface bordered by a widened base 38a, 38b positioned substantially adjacent to the grooves 14a, 14b and proximal to the bottom panel 22 of the support member 12. The flexion members 36a, 36b taper away from the bottom panel 22 and the grooves 14a, 14b in the direction of the longitudinal edges 28, 30. The tapered flexion members 36a, 36b preferably have a semi-circular geometry to minimize sharpened corners on the exposed edges 40a, 40b opposite the bases 38a, 38b and to maximize the surface contact area between the flexion members 36a, 36b and the support member 12. The flexion members 36a, 36b are fabricated from a sheet of material having substantially the same properties as the material forming the support member 12.

The flexion members 36a, 36b are maintained in position relative to the support member 12 while in the configuration of the kit 10 by means of a narrow flexible strap 42 substantially permanently and flexibly connecting the flexion members 36a, 36b to the support member 12. The strap 42 is integral with the flexion members 36a, 36b, being formed from the same sheet of material as the flexion members 36a, 36b. Although the material of the flexion members 36a, 36b and the support member 12 is characterized as being substantially rigid or stiffened at its full thickness, it is understood that the strap 42 is relatively more flexible than the flexion members 36a, 36b and support member 12 due to its relatively narrow width.

The integral strap 42 is joined to the flexion members 36a, 36b at the bases 38a, 38b thereof adjacent to the inner face 16 of the support member 12. The strap 42 extends from the bases 38a, 38b through the expansion apertures 32a, 32b to engage the outer face 18 of the support member 12 and extend around the bottom panel 22. The strap 42 is aligned with the slits 26a, 26b in the support member 12 and is substantially permanently attached to the support member 12 by means of a rivet 44 centrally positioned on the support member 12 and extending therethrough from the inner face 16 to the outer face 18.

Although the preferred configuration of the strap 42 has been described above, it is understood that other configurations of straps connecting the flexion members 36a, 36b to the support member 12 are within the scope of the present invention. For example, two separate straps can be attached to the support member 12, each strap separately connecting a respective flexion member 36a, 36b to the support member 12. Additionally, the strap or straps can be externally attached to the flexion members 36a, 36b by substantially permanent means, such as rivets, rather than being integral therewith. Likewise, the strap or straps can be integral with the support member 12, rather than externally attached thereto.

Two pairs of substantially rectangular adhesive fasteners 46a, 46b and 48a, 48b, partially shown in FIG. 1, are provided at the interface of the flexion member 36a and the first side panel 20 and at the interface of the flexion member 36b and the second side panel 24. One pair of fasteners 46a, 46b is positioned on either side of the slit 26a, and the other pair of fasteners 48a, 48b is similarly positioned with respect to the slit 26b. The preferred fasteners 46a, 46b, 48a, 48b are contact adhesives, such as segments of pressure-sensitive two-sided tape. The tape segments are fastened on one adhesive side to the inner face 16 of the support member 12 at the side panels 20, 24. The other adhesive side of the tape segment remains unfastened, being protected from adhesion to the flexion members 36a, 36b by a removable shield 50 of coated paper or a similar material positioned over the unfastened adhesive side. It is understood that the fasteners 46a, 46b, 48a, 48b can alternatively have one adhesive side fastened to the flexion members 36a, 36b and the other adhesive side blocked by the shield 50 from adhesion to the side panels 20, 24, within the scope of the present invention.

Although not shown, it is alternatively within the purview of the skilled artisan to modify the kit 10 by positioning the fasteners 46a, 46b, 48a, 48b and flexion members 36a, 36b at corresponding locations on the outer face 18 of the support member 12. This alternate construction obviates threading the strap 42 through the expansion apertures 32a, 32b and fully exposes the flexion members 36a, 36b without obstruction from the support member 12.

The kit 10 is further provided with a pliant compressible planar pad 52 overlying the inner face 16 of the support member 12. The pad 52 can be fastened to the inner face 16 at one or more points by a conventional adhesive such as glue. The pad 52 is preferably only fastened to the inner face 16 of the support member 12 at the bottom panel 22 so that the pad 52 can be folded away from the first and second side panels 20, 24 to expose them, as well as the flexion members 36a, 36b, thereby facilitating assembly of a knee splint from the kit 10 as described hereafter.

The pad 52 is preferably formed from a sheet of an inexpensive lightweight synthetic foam having a thickness on the order of about ¼ inch or more. The pad 52 can be cut in a single unitary piece from the desired sheet of material. The pad 52 is configured with a pair of longitudinal slits 54a, 54b formed therethrough in substantial alignment with the grooves 14a, 14b of the support member 12. The slits 54a, 54b segregate the pad 52 into three panels 56a, 56b, 56c. The panels 56a, 56b, 56c, however, are substantially smaller than the corresponding panels 20, 22, 24 of the support member 12, covering only a portion thereof. The panels 56a and 56c cover the flexion members 36a, 36b, while exposing a substantial portion of the side panels 20, 24. The panel 56b is substantially larger than the panels 56a, 56c and covers a portion of the bottom panel 22. A discontinuity is provided in each of the slits 54a, 54b forming bridges 58a, 58b that connect the panels 56a and 56c to the panel 56b. The bridges 58a, 58b substantially align with the expansion apertures 32a, 32b of the support member 12. The pad 52 is similarly provided with expansion apertures 60 at the intersection of the bridges 58a, 58b and the slits 54a, 54b.

FIG. 1 shows a single folded pliant belt 62 positioned in alignment with a belt loop 34 on the support member 12. Although not shown, a plurality of substantially identical folded pliant belts 62 are provided in alignment with each of the belt loops 34 on the support member 12. The belts 62 are preferably formed from a synthetic cloth and each is provided with a conventional hook and loop fastener commonly termed VELCRO enabling the belt 62 to be adjustably fastened onto itself. Although the belt 62 of the kit 10 is shown folded separately from the belt loop 34, it is within the scope of the present invention to fold the belts 62 of the kit 10 while threaded through their respective belt loops 34.

In practice, the planar components of the kit 10, including the support member 12, flexion members 36a, 36b, strap 42, pad 52, and belts 62, are maintained in a flattened stack as shown to facilitate efficient flat stackable storage of multiple kits 10. It is alternatively within the scope of the present invention to coil the belts 62 in a compact manner not shown, but readily apparent to the skilled artisan, and store the belts 62 separately from the remainder of the kit 10.

Figure 2:
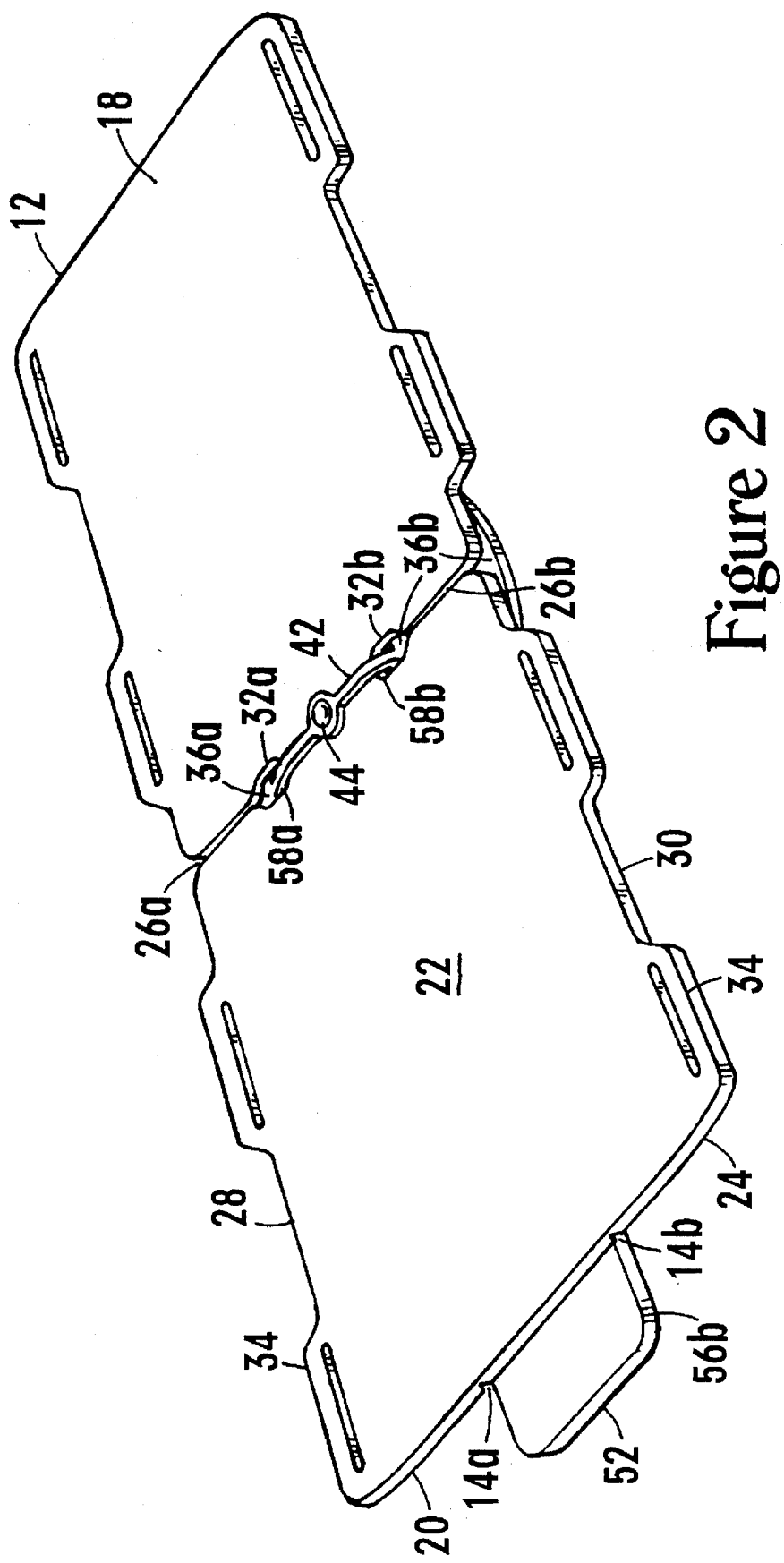
FIG. 2 is a bottom perspective view of the kit of FIG. 1.
Figure 3:
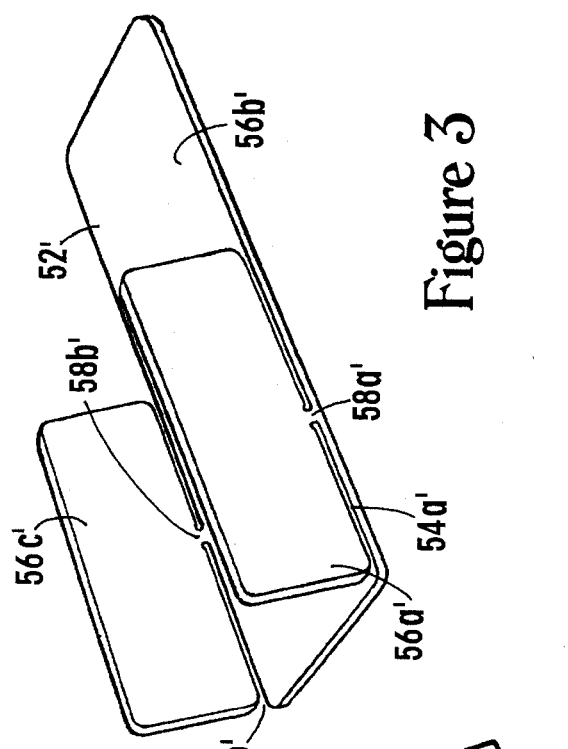
FIG. 3 is an exploded perspective view of an assembled splint of the present invention assembled from the kit of FIG. 1.
Figure 4:
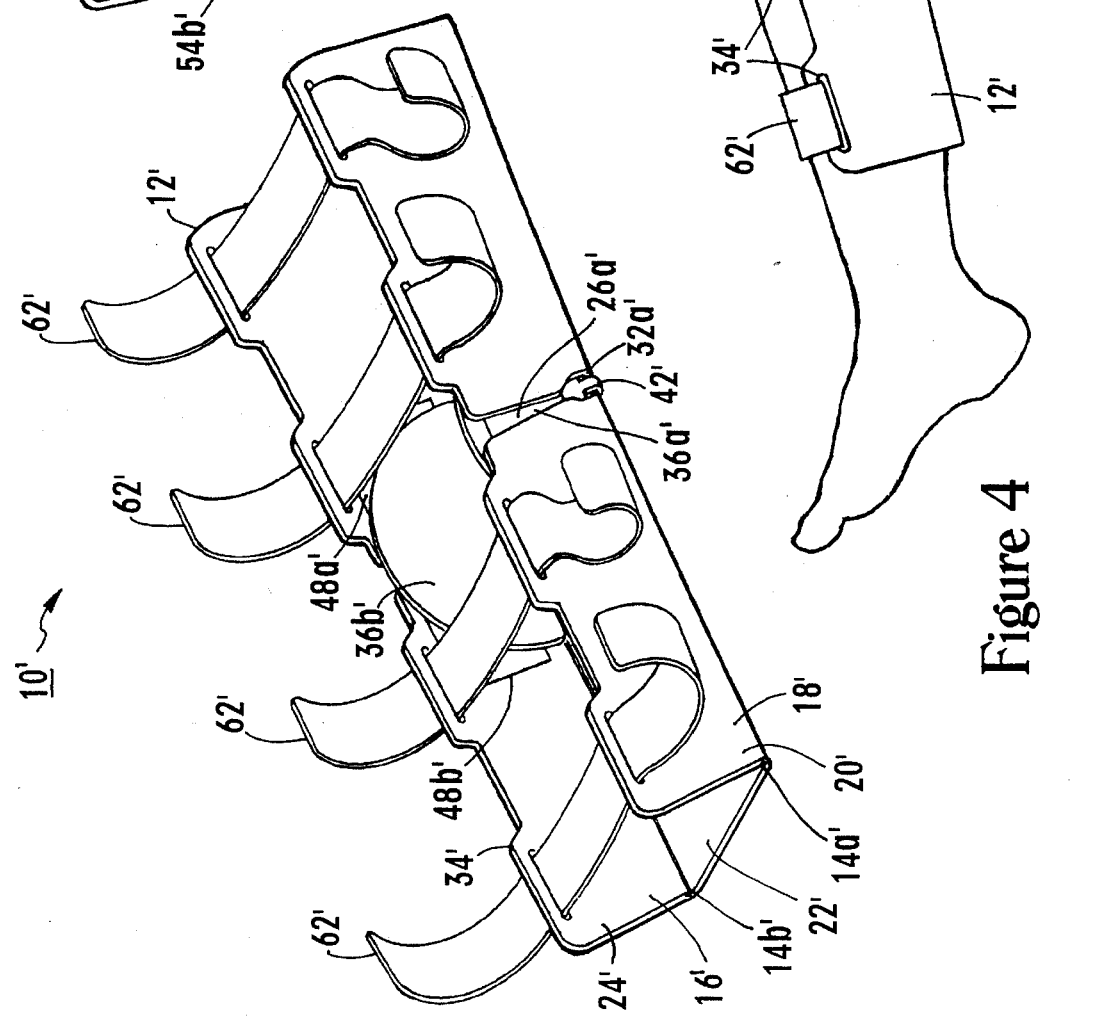
FIG. 4 is a side elevational view of the assembled splint of FIG. 3 positioned on the leg of a user.

Assembly of the kit 10 resulting in an assembled splint of the present invention, as shown and generally designated 10' in FIGS. 3 and 4, is described hereafter with reference to FIGS. 1–4. It is noted that the individual components of the unassembled kit 10 and the assembled splint 10' are virtually identical except that the substantially two-dimensional planar components of the kit 10 are manually reconfigured during assembly of the splint 10' to three dimensional components in conformance with the contours of the splinted leg. Accordingly, the components of the splint 10' in FIGS. 3 and 4 corresponding to the components of the kit 10 in FIGS. 1 and 2 are referenced by corresponding primed numerals.

The kit 10 is preferably assembled to produce the splint 10' according to one of two embodiments. In a first embodiment, the flat support member 12 is initially manually shaped to the desired leg contours away from the leg 64, using the leg 64 as a visual model, and the resulting splint 10' shown in FIG. 3 is subsequently positioned on the leg 64 to immobilize the knee joint 66. In a second embodiment, the flat support member 12 is initially positioned on the leg 64 being splinted and subsequently manually shaped to the desired leg contours, using the leg 64 as a direct form for the resulting splint 10'.

In the first embodiment, assembly of the kit 10 is initiated by pivotally bending the side panels 20, 24 upward about the grooves 14a, 14b which function as contour joints. The support member 12 inelastically deforms as it is bent about the grooves 14a, 14b to achieve a substantially U-shaped configuration having the side panels 20, 24 as the opposite sides of the "U" and the bottom panel 22 as the base of the "U". The desired flexion angle of the knee 66 being splinted is then determined and the flexion angle β of the support member 12' as shown in FIG. 4 is fixably set, wherein the flexion angle β corresponds substantially identically with the desired flexion angle of the knee joint 66.

The flexion angle β is formed in the support member 12 by pivotally separating the slits 26a, 26b of the support member 12 about the expansion apertures 32a, 32b to a separation angle α such that α=β. The slits 26a, 26b and expansion apertures 32a, 32b function in concert as flexion joints, enabling elastic deformation of the bottom panel 22 about a line through the slits 26a, 26b as the slits 26a, 26b are separated, despite the substantially rigid character of the support member 12. The flexion angle β of the resulting support member 12' is defined herein as the degree of rotation of the longitudinal axis of the distal portion 68 of the support member 12' about the line through the slits 26a, 26b relative to the longitudinal axis of the proximal portion 70 of the support member 12'. Rotation in the counterclockwise direction is defined as positive and rotation in the clockwise direction is defined as negative. The flexion angle β of the support member 12' of the splint 10' is typically a non-negative acute angle ranging from about 0° to about 60° or less.

The flexion angle β of the support member 12' is fixed by fastening the flexion members 36a, 36b to the side panels 20, 24. More particularly, the flexion angle β is fixed by folding back the pad 52 and removing the shields 50 from the fasteners 46a, 46b, 48a, 48b. Each flexion member 36a, 36b is adhered to each pair of fasteners 46a, 46b and 48a, 48b across the separated slit 26a, 26b. Thereafter, the pad 52 is replaced over the flexion members 36a, 36b. The fully-formed support member 12' as shown in FIG. 3 is slid onto the leg 64 being splinted with the pad 52' positioned therebetween. The belts 62' are tightened by cinching the belts 62' through the loops 34' and fastening the belts 62' onto themselves resulting in the splint 10' of the present invention mounted on the leg 64 as shown in FIG. 4 with the knee joint 66 substantially immobilized.

The second embodiment of assembling the kit 10 is substantially identical to the first embodiment, except that the flat support member 12 is placed on the leg 64 being splinted before, rather than after, the support member 12 is three-dimensionally reconfigured. The support member 12 is reconfigured while in position on the leg 64. Thereafter, the support member 12' and belts 62' are positioned and function in substantially the same manner as described above.

The assembled splint 10' of the present invention, as shown in FIG. 4, is designed to be retained on the leg 64 for several hours to several days as needed during the post-trauma period, thereby effectively immobilizing the knee joint 66 Thereafter, the splint 10' which is fabricated from inexpensive materials, can be readily disposed of.

An alternate embodiment of the kit of the present invention is shown and described with reference to FIG. 5, wherein the kit is generally designated 100. The kit 100 is particularly applicable to elbow splints that fit onto the arm of a user for immobilizing the elbow joint and to ankle splints that fit onto the leg of a user for immobilizing the ankle joint. The kit 100 is described hereafter by way of example as applicable to an ankle splint. It is apparent to one skilled in the art, however, that the kit 100 can alternatively be adapted to body parts encompassing a flexible body joint other than the ankle in accordance with the instant teaching.

The kit 100 comprises a support member 120 fabricated from a sheet of material in substantially the same manner and having substantially the same properties as described above with respect to the kit 10. The support member 120 has a pair of longitudinal grooves 140a, 140b provided in the inner face 160 of the support member 120 segmenting the support member 120 into a first side panel 200, a bottom panel 220, and a second side panel 240. A pair of slits 260a, 260b are also provided in the support member 120. The slits 260a, 260b are intermediately positioned on the longitudinal edges 280, 300 of the support member 120, respectively, and are aligned approximately perpendicular to the longitudinal axis of the support member 120. Unlike the slits 26a, 26b of the kit 10, however, the present slits 260a, 260b are V-shaped rather than linear.

An opening 322 is formed through the bottom panel 220 in alignment with the slits 260a, 260b to facilitate elastic deformation of the support member at the slits 260a, 260b and to receive the olecranon of the elbow as is described hereafter. In addition, a plurality of longitudinal belt loops 340 are integrally formed in the support member 120 along the longitudinal edge 280 and correspondingly along the longitudinal edge 300 of the support member 120. A proximal belt loop 342 is also integrally formed in the support member 120 at the proximal end 344 thereof.

The kit 100 further comprises an extension member 346 sized and configured to slidably fit within the distal end 348 of the support member 120 and adjustably extend the length of the distal end 348. The extension member 346 is fabricated from a sheet of material having substantially the same properties as the material forming the support member 120. The extension member 346 has longitudinal grooves 350a, 350b and panels 352a, 352b, 352c corresponding to those of the support member 120. The extension member is further provided with longitudinal belt loops 354 in the manner of the extension member 120. A fastener 356, such as a length of shielded two-sided tape, is positioned on the inner face 160 of the bottom panel 220 to fixably fasten the extension member 346 to the support member 120 as desired.

The kit 100 still further comprises a pair of flexion members 360a, 360b associated with the slits 260a, 260b, respectively. The flexion members 360a, 360b have a planar, tapered configuration. In accordance therewith, each flexion member 360a, 360b has a narrowed base 380a, 380b positioned substantially adjacent to the grooves 140a, 140b and proximal to the bottom panel 220 of the support member 120. The flexion members 360a, 360b taper toward the bottom panel 220 and the grooves 140a, 140b in a direction away from the longitudinal edges 280, 300. The tapered flexion members 360a, 360b preferably have a trapezoidal geometry to cover the V-shaped slits 260a, 260b. The flexion members 360a, 360b are fabricated from a sheet of material having substantially the same properties as the material forming the support member 120.

The flexion members 360a, 360b are maintained in position relative to the support member 120 while in the configuration of the kit 100 by means of narrow flexible straps 420a, 420b substantially permanently and flexibly connecting the flexion members 360a, 360b to the support member 120. The straps 420a, 420b are integral with the support member 120, being formed from the same sheet of material as the support member 120 and extending from the support member 120 to the flexion members 360a, 360b at the position of the slits 260a, 260b. The straps 420a, 420b are slidably connected to the flexion members 360a, 360b by means of rivets 422a, 422b fixably engaging the straps 420a, 420b and slidably engaging slots 424a, 424b formed in the flexion members 360a, 360b. Although the preferred configuration of the straps 420a, 420b has been described above, it is understood that other configurations of straps connecting the flexion members 360a, 360b to the support member 120 are within the scope of the present invention.

A pair of adhesive fasteners (not shown) are provided on the back side of each flexion member 360a, 360b to engage the inner face 160 of the first and second side panels 200, 240 on both sides of the slits 260a, 260b when the splint is assembled as described hereafter. Although not shown, it is alternatively within the purview of the skilled artisan to modify the kit 100 by positioning the fasteners at corresponding locations on the front side of the flexion members 360a, 360b to engage the outer face of the first and second side panels 200, 240.

The kit 100 is further provided with a pliant compressible planar pad 520 overlying the inner face 160 of the support member 120. The pad 520 is fabricated from the same material in substantially the same manner as described above with respect to the kit 10. The pad 520, however, has an hourglass configuration to more readily conform to the contours of the arm and elbow joint.

Figure 5:
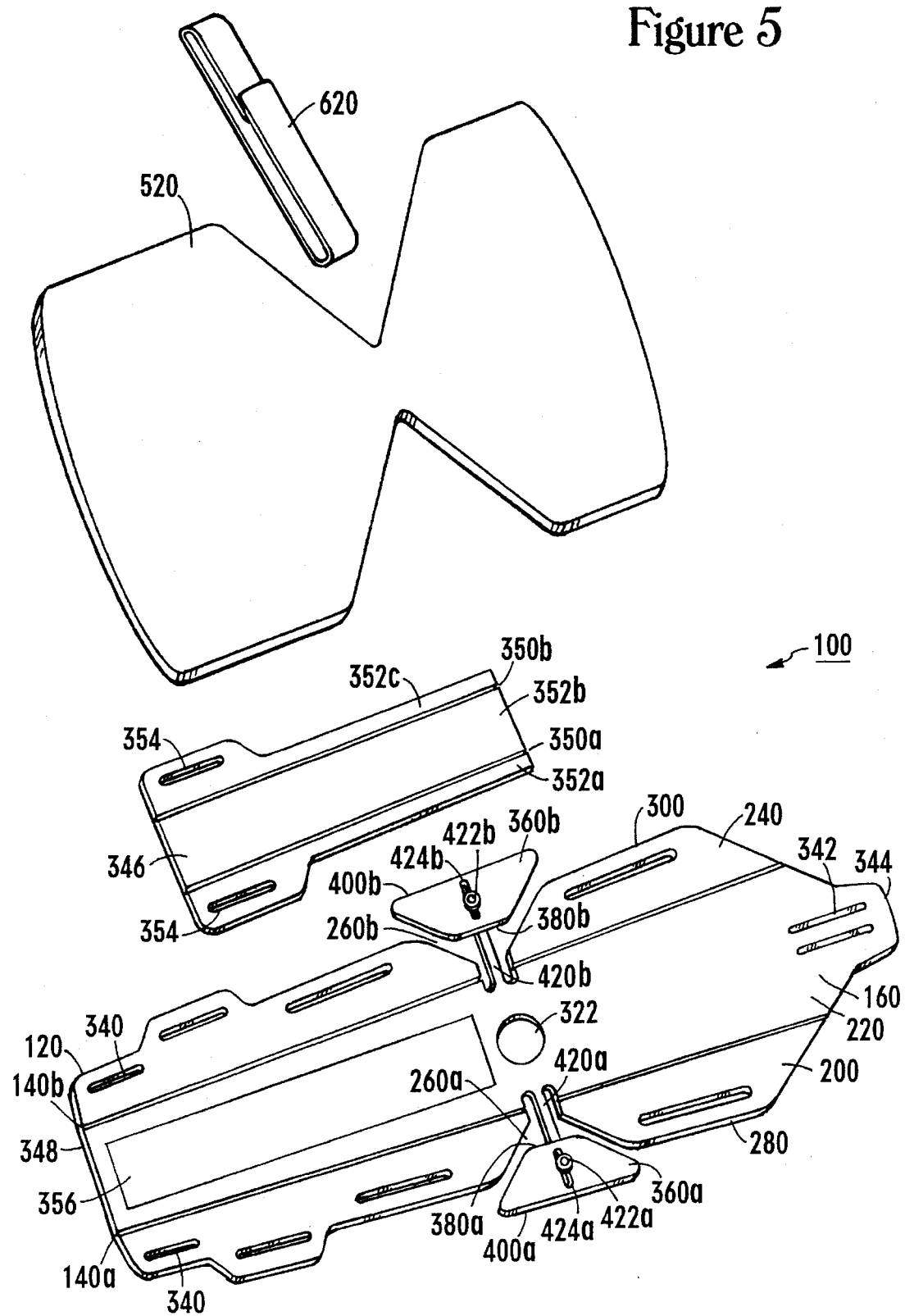
FIG. 5 is an exploded top perspective view of an alternate embodiment of an unassembled flat stackable kit of the present invention from which a splint is assembled.

FIG. 5 shows a single folded pliant belt 620 positioned in alignment with a longitudinal belt loop 340 on the support member 120. Although not shown, a plurality of substantially identical folded pliant belts 620 are provided in alignment with each of the belt loops 340 on the support member 120. A belt 620 is similarly provided for the proximal belt loop 342. The belts 620 are substantially the same as described above with respect to the kit 10. In practice, the planar components of the kit 100, including the support member 120, flexion members 360a, 360b, straps 420a, 420b, pad 520, and belts 620, are maintained in a flattened stack as shown to facilitate efficient flat stackable storage of multiple kits 100.

Figure 6:
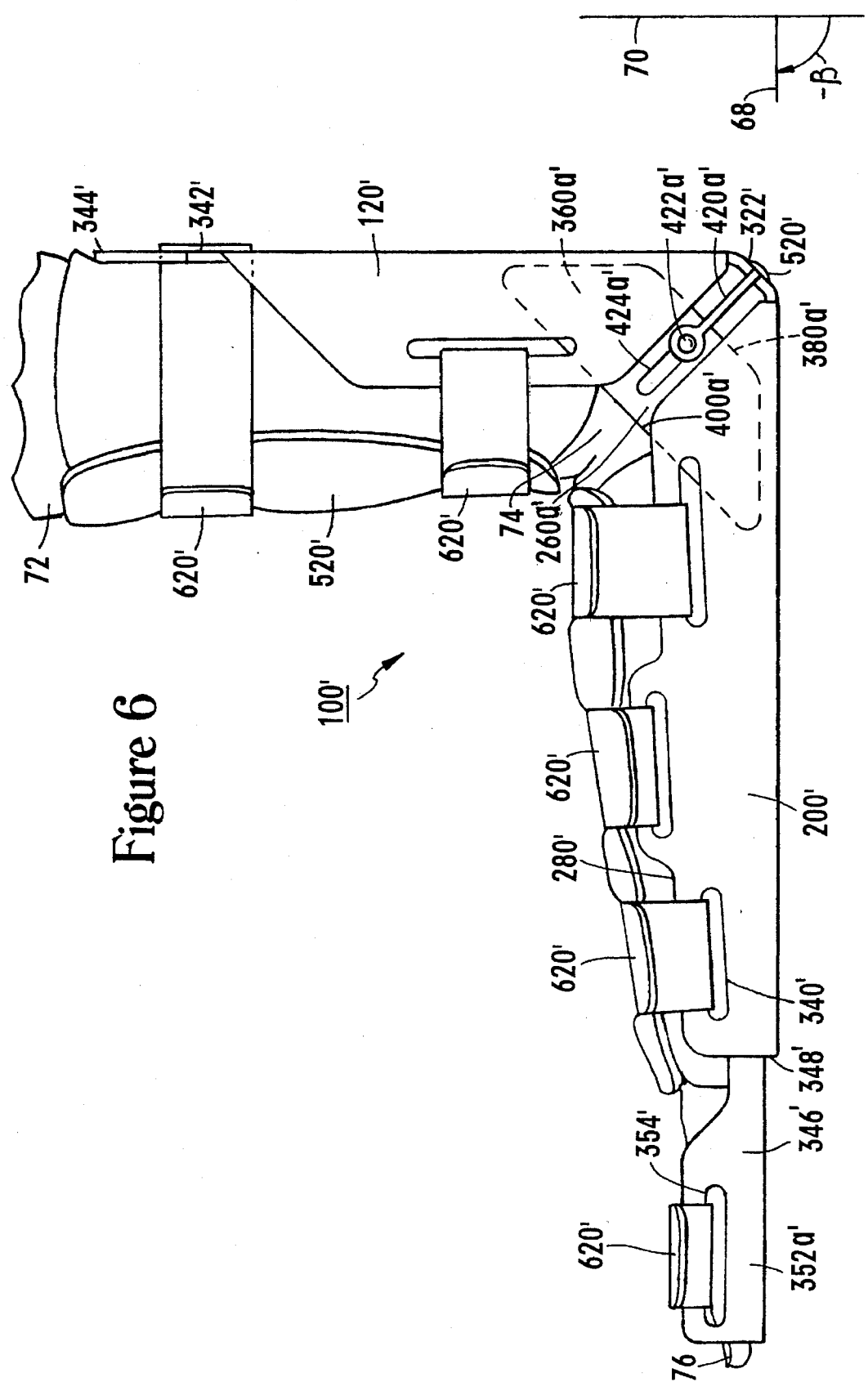
FIG. 6 is a side elevational view of the assembled splint of FIG. 5 positioned on the arm of a user.

Assembly of the kit 100 resulting in an alternate embodiment of an assembled splint of the present invention, as shown and generally designated 100' in FIG. 6, is described hereafter with reference to FIGS. 5 and 6. The individual components of the unassembled kit 100 and the assembled splint 100' are virtually identical except that the substantially two-dimensional planar components of the kit 100 are manually reconfigured during assembly of the splint 100' to three dimensional components in conformance with the contours of the splinted arm. Accordingly, the components of the splint 100' in FIG. 6 corresponding to the components of the kit 100 in FIG. 5 are referenced by corresponding primed numerals.

The kit 100 is assembled to produce the splint 100' in substantially the same manner as described above with respect to the kit 10 and the splint 10'. Since the splint 100' is specifically adapted to the arm 72 and elbow joint 74, however, the flexion angle β is formed in the support member 120 by pivotally converging the sides of the V-shaped slits 260a, 260b together and thereafter fixing the flexion angle β by fastening the flexion members 36a, 36b to the support member 120. The flexion angle β of the support member 120' of the splint 100' is typically a non-positive angle ranging from about 0° to about −90° or more. In assembling the splint 100', the extension length of the extension member 346 is adjusted and fixed by the fastener 356 in correspondence with the length of the arm 72 being splinted. The extension member 346 preferably supports the hand 76.

While the forgoing preferred embodiments of the invention have been described and shown, it is understood that alternatives and modifications, such as those suggested and others, may be made thereto and fall within the scope of the invention.

We claim:

1. A flat stackable kit for a splint in a disassembled state comprising:

a support member for a body part of a user being splinted having an elongated substantially planar surface;

a contour joint formed substantially longitudinally in said support member surface and flattened in a fully extended position;

a flexion joint formed substantially perpendicular to said contour joint in said support member surface and flattened in a fully extended position;

a flexion member having a substantially planar surface sized to be extendable across at least a portion of said flexion joint when said kit is assembled as the splint;

a flexible strap connecting said flexion member to said support member; and a fastener positioned on said flexion member or said support member for fastening said flexion member surface to said support member surface across said flexion joint when said kit is assembled as the splint.

2. A flat stackable kit for a splint as recited in claim 1 wherein said fastener is an adhesive positioned on said support member surface or said flexion member surface.

3. A flat stackable kit for a splint as recited in claim 2 further comprising a non-adhesive shield covering said adhesive.

4. A flat stackable kit for a splint as recited in claim 1 wherein said contour joint is a groove formed in said support member surface.

5. A flat stackable kit for a splint as recited in claim 1 wherein said flexion member is a first flexion member and said flexion joint is a first flexion joint, said kit further comprising a second flexion member and a second flexion joint, said second flexion member being connected to said support member by said strap and having a substantially planar surface sized to be extendable across at least a portion of said second flexion joint when said kit is assembled as the splint.

6. A flat stackable kit for a splint as recited in claim 1 wherein said strap is integral with said flexion member.

7. A flat stackable kit for a splint as recited in claim 5 wherein said strap is integral with said first and second flexion members.

8. A flat stackable kit for a splint as recited in claim 1 wherein said flexion joint includes a slit and an expansion aperture.

9. A flat stackable kit for a splint as recited in claim 8 wherein said strap extends through said expansion aperture.

10. A flat stackable kit for a splint as recited in claim 1 further comprising a substantially planar flexible pad positionable on said support member surface.

11. A flat stackable kit for a splint as recited in claim 1 wherein said strap is integral with said support member.

12. A flat stackable kit for a splint as recited in claim 1 wherein said flexion member has a slot formed therein.

13. A flat stackable kit for a splint as recited in claim 12 wherein said strap has means for slidably connecting said strap to said slot.

14. A flat stackable kit for a splint as recited in claim 1 wherein said flexion member is tapered toward said contour joint.

15. A flat stackable kit for a splint as recited in claim 1 wherein said flexion member is tapered away from said contour joint.

16. A splint comprising:
    a support member for a body part having an elongated surface;
    a contour joint formed substantially longitudinally in said support member surface, said support member surface pivoted about said contour joint at a contour angle;
    a flexion joint formed substantially perpendicular to said contour joint in said support member surface, said support member surface pivoted about said flexion joint at a flexion angle;
    a flexion member having a flexion member surface positioned across at least a portion of said flexion joint;
    a flexible strap flexibly connecting said flexion member to said support member; and
    a fastener positioned on said flexion member or said support member for fastening said flexion member surface to said support member surface across said flexion joint, thereby maintaining said flexion angle substantially fixed.

17. A splint as recited in claim 16 wherein said fastener is an adhesive positioned on said support member surface or said flexion member surface.

18. A splint as recited in claim 16 wherein said flexion member is a first flexion member and said flexion joint is a first flexion joint, said splint further comprising a second flexion member and a second flexion joint, said second flexion member being connected to said support member by said strap and having a substantially planar surface positioned across at least a portion of said second flexion joint.

19. A splint as recited in claim 16 wherein said strap is integral with said flexion member.

20. A splint as recited in claim 18 wherein said strap is integral with said first and second flexion members.

21. A splint as recited in claim 16 wherein said flexion joint includes a slit and an expansion aperture in said support member surface.

22. A splint as recited in claim 21 wherein said strap extends through said expansion aperture.

23. A splint as recited in claim 16 further comprising a substantially planar flexible pad positioned on said support member surface.

24. A splint as recited in claim 16 wherein said strap is integral with said support member.

25. A splint as recited in claim 16 wherein said flexion member has a slot formed therein.

26. A splint as recited in claim 25 wherein said strap has means for slidably connecting said strap to said slot.

27. A splint as recited in claim 16 wherein said flexion member is tapered toward said contour joint.

28. A splint as recited in claim 16 wherein said flexion member is tapered away from said contour joint.

29. A splint as recited in claim 16 wherein said contour joint is a groove formed in said support member surface.

30. A splint as recited in claim 21 wherein said slit is substantially linear.

31. A splint as recited in claim 21 wherein said slit is substantially V-shaped.

* * * * *